United States Patent [19]

Saji et al.

[11] Patent Number: 4,461,774

[45] Date of Patent: Jul. 24, 1984

[54] ANTIFUNGAL IMIDAZOLYLCARBOXYLIC ACIDS AND THEIR DERIVATIVES

[75] Inventors: Ikutaro Saji; Hiroshi Yamazaki; Shunji Aono, all of Osaka; Katsuaki Ichise, Kyoto; Takao Okuda, Osaka, all of Japan

[73] Assignee: Sumitomo Chemical Company, Limited, Osaka, Japan

[21] Appl. No.: 427,558

[22] Filed: Sep. 29, 1982

[30] Foreign Application Priority Data

Oct. 9, 1981 [JP] Japan ................. 56-161413

[51] Int. Cl.³ .................. A01N 43/50; C07D 233/60
[52] U.S. Cl. ................ 424/273 R; 548/336; 548/341
[58] Field of Search ............ 548/341; 424/273 R

[56] References Cited

U.S. PATENT DOCUMENTS 4,315,023 2/1982 Partyka et al. ............... 548/341 X

FOREIGN PATENT DOCUMENTS 54974 6/1982 European Pat. Off. .......... 548/341
55833 7/1982 European Pat. Off. .......... 548/341
2434155 3/1980 France ................... 548/341

OTHER PUBLICATIONS

March, J., *Advanced Organic Chemistry*, McGraw Hill, New York, 1968, pp. 328–329.

*Primary Examiner*—Richard A. Schwartz
*Attorney, Agent, or Firm*—Birch, Stewart, Kolasch & Birch

[57] ABSTRACT

An imidazolylcarboxylic acid compound of the formula:

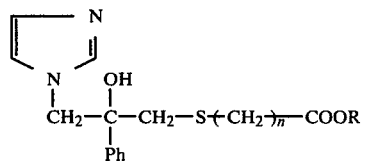

wherein Ph is a phenyl group or a phenyl group substituted with one or two halogen atoms, R is a hydrogen atom or a $C_1$–$C_8$ alkyl group and n is an integer of 1 to 8, which is useful as an antifungal agent.

13 Claims, No Drawings

ANTIFUNGAL IMIDAZOLYLCARBOXYLIC ACIDS AND THEIR DERIVATIVES

The present invention relates to imidazolylcarboxylic acid and their derivatives, the production and use thereof.

The imidazolylcarboxylic acids and their derivatives of the invention are representable by the formula:

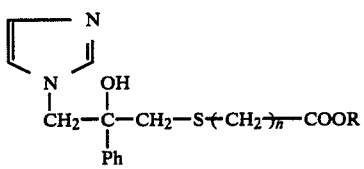   (I)

wherein Ph is a phenyl group or a phenyl group substituted with one or two halogen atoms, R is a hydrogen atom or a $C_1$–$C_8$ alkyl group and n is an integer of 1 to 8. Other compounds within the invention include compounds wherein Ph is a phenyl group substituted with one or two halogen atoms, R is a hydrogen atom or a $C_1$–$C_4$ alkyl group and n is an integer of 1 to 4.

In the above significances, the term "$C_1$–$C_8$ alkyl" is intended to mean a straight or branched alkyl group having 1 to 8 carbon atoms (e.g. methyl, ethyl, n-propyl, isopropyl, n-butyl, isobutyl, t-butyl, n-pentyl, n-hexyl, n-octyl). The term "halogen" covers fluorine, chlorine, bromine and iodine.

The imidazolylcarboxylic acid compounds of the invention may be prepared in either an optically active form or a racemic form. Thus, the scope of the invention is not limited to the racemic form but also encompasses the individual optical isomers.

Among various imidazolylcarboxylic acid compounds represented by the formula (I), preferred are those wherein Ph is a phenyl group substituted with one or two chlorine atoms, R is a hydrogen atom or a $C_1$–$C_4$ alkyl group and n is an integer of 1 to 4.

The said imidazolylcarboxylic acid compounds of the formula (I) wherein R is a $C_1$–$C_8$ alkyl group can be prepared, for instance, by reacting an epoxide compound of the formula:

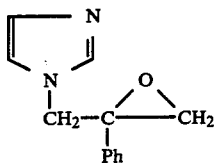   (II)

wherein Ph is as defined above, with a thiol compound of the formula:

   (III)

wherein $R_1$ is a $C_1$–$C_8$ alkyl group and n is as defined above.

Usually, the thiol compound (III) is employed in a metallized form with an alkali metal at the terminal hydrogen atom. The amount of the thiol compound (III) may be usually from 1 to 2 molar equivalents with respect to the epoxide compound (II).

The reaction may be carried out, usually in an inert solvent, at a temperature of from 0° C. to the refluxing temperature of the reaction mixture, preferably of from 0° C. to room temperature. As the inert solvent, there may be used an aliphatic hydrocarbon (e.g. hexane), an aromatic hydrocarbon (e.g. benzene, toluene, xylene), an ether (e.g. dioxane, tetrahydrofuran), acetonitrile, dimethylformamide, dimethylsulfoxide, etc.

The starting epoxide compound (II) may be prepared, for instance, by reacting a ketone compound of the formula:

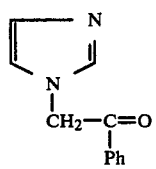

wherein Ph is as defined above with dimethylsulfoxionium methylide (($CH_3)_2\overset{+}{S}OCH_2$) in an inert solvent such as dimethylsulfoxide at a temperature of 0° to 100° C. (J. Am. Chem. Soc., 87, 1353 (1965)). The said ketone compound is per se known or can be produced by a per se conventional procedure (Japanese Patent Publication (examined) No. 39665/1975).

The metallized form of the thiol compound (III) may be prepared, for instance, by reacting the thiol compound (III) with an equimolar amount of sodium hydride, metallic potassium or n-butyl lithium in a suitable solvent.

The imidazolylcarboxylic acid compounds of the formula (I) wherein R is a $C_1$–$C_8$ alkyl group is, if desired, hydrolyzed in an aqueous alkali metal hydroxide solution to yield the corresponding free acid, i.e. the imidazolylcarboxylic acid compound of the formula (I) wherein R is a hydrogen atom. As the solvent, there may be used water, an alcohol (e.g. methanol), an ether (e.g. dioxane, tetrahydrofuran), dimethylformamide, dimethylsulfoxide, etc. As the alkali metal hydroxide, there may be used sodium hydroxide, potassium hydroxide, lithium hydroxide, etc. The amount of the alkali metal hydroxide may be from 1 to 5 molar equivalents with respect to the ester. The reaction temperature is normally from 0° to 100° C.

The imidazolylcarboxylic acid compounds (I) exhibit a remarkable antimicrobial activity against various microorganisms, particularly fungi. Also, some of them show antifungal activity against phytopathogenic fungi.

The in vivo test of the antifungal activity with some representatives of the imidazolylcarboxylic acid compounds (I) was carried out in the following manner:

*Candida albicans* KB-8 was cultured on a Sabroud's agar plate admixed with blood in a concentration of 5% by weight at 30° C. for 4 days and suspended in physiological saline solution to make a number of cells of $10^7$/ml. The suspension was intravenously injected into DDY strain male mice of 5 weeks old at a dose of 0.2 ml per mouse through the tail vein.

The animals were orally medicated with the test compound in the form of 2% by weight methylcellulose suspension at a total dose of 20 mg per kg of the body weight immediately and 5 hours after the infection.

After 24 hours from the infection, the animals were sacrificed, and the kidneys were taken out. After diluting with physiological saline solution, the dilution was centrifuged at 900 rpm for 5 minutes. A certain amount of the supernatant was scattered on a Sabroud's agar plate and cultured at 37° C. for 48 hours. Then, the number of colonies was counted, the number of cells per one gram of the kidney was calculated, and the difference between the calculated numbers in the medicated group and in the non-medicated group was expressed by a logarithmic value. The results are shown below.

solid pharmaceutical preparations such as tablets, capsules, powders or granules, or in the form of conventional liquid pharmaceutical preparations such as suspensions, emulsions or solutions. The daily dosage may vary depending upon the administration route and is

TABLE 1

Antifungal activity in vivo (Decreases of cells in the kidney of Candida-infected mice)

Imidazolylcarboxylic acid compound (I)

$$\text{CH}_2-\underset{\underset{\text{Ph}}{|}}{\overset{\overset{\text{OH}}{|}}{\text{C}}}-\text{CH}_2-\text{S}+\text{CH}_2\overset{}{)_n}\text{COOR}$$

with N-imidazolyl attached to the CH₂

| Ph | R | n | Dose (per os, mg/kg) | Medicated group, number of cells in kidney (cell/g) | Non-medicated group, number of cells in kidney (cell/g) | Medicated/Non-medicated (logarithmic value) |
|---|---|---|---|---|---|---|
| 2,4-dichlorophenyl | $C_2H_5$ | 1 | 20 | $2.52 \times 10^3$ | $1.82 \times 10^5$ | −1.86 |
| 2,4-dichlorophenyl | H | 1 | 20 | $5.59 \times 10^3$ | $1.82 \times 10^5$ | −1.51 |
| 2,4-dichlorophenyl | $C_2H_5$ | 3 | 20 | $2.69 \times 10^3$ | $7.75 \times 10^4$ | −1.46 |
| 2,4-dichlorophenyl | $C_2H_5$ | 4 | 20 | $1.27 \times 10^4$ | $7.75 \times 10^4$ | −0.79 |
| 2,4-dichlorophenyl | H | 4 | 20 | $1.52 \times 10^4$ | $7.75 \times 10^4$ | −0.71 |
| 2,4-dichlorophenyl | H | 3 | 20 | $1.70 \times 10^3$ | $1.82 \times 10^5$ | −2.03 |
| Miconazole*[1] | | | 100 | $2.96 \times 10^4$ | $1.86 \times 10^5$ | −0.80 |

Note:
*[1] 1-[2,4-Dichloro-β-(2,4-dichlorobenzyloxy)phenylethyl]imidazole (nitrate).

As understood from the above results, the imidazolylcarboxylic acid compounds (I) show an excellent antifungal activity.

Advantageously, the imidazolylcarboxylic acid compounds (I) are quite low in toxicity, and their $LD_{50}$ values are more than 500 mg/kg when determined by the oral route in mice. Thus, they are useful as antifungal agents.

The imidazolylcarboxylic acid compounds (I) can be administered parenterally, orally or locally to warm-blooded animals and human beings in the form of conventional pharmaceutical preparations. For instance, they can be administered in the form of conventional usually between 10 mg and 5 g for human beings.

Practical and presently preferred embodiments of the invention are illustratively shown in the following examples, which are not intended to limit the scope of the invention thereto.

EXAMPLE 1

To a solution of ethyl 2-mercaptoacetate (2.1 g) in 1,2-dimethoxyethane (30 ml) kept at 0°–10° C., 65% sodium hydride (720 mg) was portionwise added, and the mixture was stirred at room temperature for 1 hour.

2-(2,4-Dichlorophenyl)-2-[(imidazol-1-yl)methyl]oxirane (4.0 g) was added thereto, followed by stirring at 5°–20° C. for 4 hours. The reaction mixture was poured onto ice water (50 ml) and extracted with chloroform. The chloroform extract was washed with water, dried and evaporated to remove the solvent. The oily residue was purified by silica gel chromatography to give a crystalline mass (1.7 g). Recrystallization from ether gave ethyl 1-[2-(2,4-dichlorophenyl)-2-hydroxy-3-(imidazol-1-yl)propylthio]acetate (1.44 g). Yield, 25.1%. M.P., 93°–94° C.

Elementary analysis: Calcd. for $C_{16}H_{18}N_2O_3Cl_2S$: C, 49.24%; H, 4.65%; N, 7.17%. Found: C, 49.50%; H, 4.59%; N, 7.07%.

EXAMPLE 2

A mixture of ethyl 1-[2-(2,4-dichlorophenyl)-2-hydroxy-3-(imidazol-1-yl)propylthio]acetate (500 mg) and 1N aqueous sodium hydroxide solution (20 ml) was stirred at 80° C. for 1 hour. The reaction mixture was neutralized by adding 1N hydrochloric acid (20 ml) and then purified by resin chromatography to give 1-[2-(2,4-dichlorophenyl)-2-hydroxy-3-(imidazol-1-yl)propylthio]acetic acid (305 mg). Yield, 64.8%. M.P., 198°–200° C.

Elementary analysis: Calcd. for $C_{14}H_{14}N_2O_3Cl_2S$: C, 46.07%; H, 3.91%; N, 7.75%. Found: C, 45.88%; H, 3.88%; N, 7.64%.

EXAMPLE 3

To a solution of ethyl 4-mercaptobutyrate (20.5 g) in 1,2-dimethoxyethane (200 ml) kept at 0°–10° C., 65% sodium hydride (5.82 g) was portionwise added, and the mixture was stirred at room temperature for 1 hour. 2-(2,4-Dichlorophenyl)-2-(imidazol-1-yl)methyloxirane (27.1 g) was added thereto, followed by stirring at 20°–25° C. for 3 hours. The reaction mixture was poured onto ice water and extracted with chloroform. The chloroform extract was washed with water, dried and evaporated to remove the solvent. The oily residue was crystallized from ether, and then recrystallized from a mixture of ether and chloroform to give ethyl 1-[2-(2,4-dichlorophenyl)-2-hydroxy-3-(imidazol-1-yl)propylthio]butyrate (28.7 g). Yield, 66.1%. M.P., 92°–93° C.

Elementary analysis: Calcd. for $C_{18}H_{22}N_2O_3Cl_2S$: C, 51.80%; H, 5.28%; N, 6.71%. Found: C, 52.05%; H, 5.23%; N, 6.62%.

EXAMPLES 4 AND 5

In the same manner as in Example 1 or 3, the following compounds were produced:

| Example No. | Product | Physical data |
| --- | --- | --- |
| 4 | Methyl 1-[2-(2,4-dichlorophenyl)-2-hydroxy-3-imidazol-1-yl)propylthio]propionate | M.P., 94–97° C. |
| 5 | Ethyl 1-[2-(2,4-dichlorophenyl-2-hydroxy-3-imidazol-1-yl)propylthio]pentanoate | M.P., 56–58° C. |

EXAMPLES 6 AND 7

In the same manner as in Example 2, the following compounds were produced:

| Example No. | Product | Physical data |
| --- | --- | --- |
| 6 | 1-[2-(2,4-Dichlorophenyl)-2-hydroxy-3-(imidazol-1-yl)propylthio]pentanoic acid | Amorphous powder; Mass spectrum M/e: 403 (M+) |
| 7 | 1-[2-(2,4-Dichlorophenyl)-2-hydroxy-3-(imidazol-1-yl)propylthio]butyric acid | M.P., 101–102° C. |

EXAMPLE 8

The reaction was carried out in the same manner as in Example 3 but using (−)-2-(2,4-dichlorophenyl)-2-(imidazol-1-yl)methyloxirane (M.P., 107°–108.5° C.; $[\alpha]_D^{21.5}$, −8.4° (C=1.0, MeOH) in place of (±)-2-(2,4-dichlorophenyl)-2-(imidazol-1-yl)methyloxirane. The obtained oily residue was dissolved in ether, and hydrochloric acid was added thereto. The precipitated crystals were collected by filtration and recrystallized from ethyl acetate to give (−)-ethyl 1-[2-(2,4-dichlorophenyl)-2-hydroxy-3-(imidazol-1-yl)propylthio]butyrate hydrochloride. Yield, 71.3%. M.P., 123.0°–124.0° C. $[\alpha]_D^{20.0}$, −76.2° (C=1.0, MeOH).

Elementary analysis for $C_{12}H_{23}N_2O_3Cl_3S$ (%): Calcd.: C, 47.64; H, 5.11; N, 6.17; S, 7.07; Cl, 23.44. Found: C, 47.46; H, 5.09; N, 6.10; S, 7.38; Cl, 23.09.

EXAMPLE 9

The reaction was carried out in the same manner as in Example 8 but using (+)-2-(2,4-dichlorophenyl)-2-(imidazol-1-yl)methyloxirane (M.P., 107°–108.5° C.; $[\alpha]_D^{24}$, +8.8° (C=1.0, MeOH) in place of the (−)-stereoisomer to give (+)-ethyl 1-[2-(2,4-dichlorophenyl)-2-hydroxy-3-(imidazol-1-yl)propylthio]butyrate hydrochloride in 76.2% yield. M.P., 123.0°–124.5° C. $[\alpha]_D^{24}$, +77.1° (C=1.0, MeOH).

EXAMPLE 10

The reaction was carried out in the same manner as in Example 2 but using (−)-ethyl 1-[2-(2,4-dichlorophenyl)-2-hydroxy-3-(imidazol-1-yl)propylthio]butyrate hydrochloride in place of (±)-ethyl 1-[2-(2,4-dichlorophenyl)-2-hydroxy-3-(imidazol-1-yl)propylthio]acetate to give (−)-1-[2-(2,4-dichlorophenyl)-2-hydroxy-3-(imidazol-1-yl)propylthio]-butyric acid as an amorphous powder in 59.8% yield. M.P., 55°–61° C. $[\alpha]_D^{20}$, −70.0° (C=1.0, MeOH).

EXAMPLE 11

In the same manner as in Example 10, (+)-1-[2-2,4-dichlorophenyl)-2-hydroxy-3-(imidazol-1-yl)propylthio]butyric acid was produced. Yield, 65%. M.P., 57°–61° C. (amorphous powder). $[\alpha]_D^{20}$+70.0° (C=1.0, MeOH).

(−)-2-(2,4-Dichlorophenyl)-2-(imidazol-1-yl)-methyloxirane and (+)-2-(2,4-dichlorophenyl)-2-(imidazol-1-yl)methyloxirane used as the starting materials in Examples 8 and 9 were produced in the following manner.

REFERENCE EXAMPLE 1

A mixture of 2-(2,4-dichlorophenyl)-2-(imidazol-1-yl)methyloxirane (170.4 g; Japanese Patent Publications (unexamined) Nos. 12372/1981 and 106666/1982) and a 25% aqueous sulfuric acid solution (1193 g) was stirred at 80°–85° C. for 5 hours. To the reaction mixture, ethyl acetate (405 ml) and a 28% aqueous ammonia solution (520 ml) were added dropwise at 0°–10° C., and then the mixture was stirred for 1 hour at the same temperature. The resulting precipitate was collected by filtration and dried at 80° C. (10 mmHg) for 5 hours to give 2-(2,4-dichlorophenyl)-1-(imidazol-1-yl)-2,3-propanediol. Yield, 146 g; 80.3%. M.P., 123.5°–124.5° C.

Elementary analysis for $C_{12}H_{12}N_2O_2Cl_2$ (%): Calcd.: C, 50.20; H, 4.21; N, 9.75. Found: C, 49.98; H, 4.41; N, 9.69.

REFERENCE EXAMPLE 2

To an ice-cooled mixture of 2-(2,4-dichlorophenyl)-1-imidazol-1-yl)-2,3-propanediol (7 g), pyridine (2.39 g) and tetrahydrofuran (120 ml) was added a solution of (+)-2-(4-chlorophenyl)isovaleroyl chloride (6.19 g; Journal of Synthetic Organic Chemistry, Japan, 38, 1151–1162 (1980)) in tetrahydrofuran (20 ml) with stirring for 15 minutes. The reaction mixture was kept at the same temperature for 1 hour and then at room temperature for 30 minutes. The solvent was removed in vacuo below 30° C. Water was added thereto, and the solution was extracted with dichloromethane. The extract was washed with a 10% aqueous sodium hydroxide solution (20 ml) and then with water, dried over magnesium sulfate and evaporated to dryness in vacuo to give an oily residue (10.1 g).

NMR (CDCl$_3$) δ: 0.53 (3H, d, J=7 Hz), 0.75 (3H, d, J=7 Hz), 1.9–2.3 (1H, m), 2.95 (1H, d, J=10 Hz), 4.2–4.6 (2H, m), 4.80, 4.40 (each 0.5H, d, J$_{gem}$=14 Hz), 4.83, 4.38 (each 0.5 H, d, J$_{gem}$=14 Hz), 6.7–7.5 (10H).

The residue (10.1 g) was chromatographed on a silica gel column (600 g, Licroprep ® SI-60, grain size, 25–40 μm) at medium pressure with a mixed solvent (MeOH:CHCl=0.4:99.6 (v/v)). The first eluate gave (+)-3-[2-(4-chlorophenyl)isovaleroyloxy]-2-(2,4-dichlorophenyl)-1-(imidazol-1-yl)-2-propanol (3.5 g) as colorless prisms. Yield, 34.7%. M.P., 145°–146.5° C. $[α]_D^{27}$, +60.5° (C=1.0, MeOH).

Elementary analysis for $C_{23}H_{23}Cl_3N_2O_3$ (%):
Calcd.: C, 57.34; H, 4.78; N, 5.82. Found: C, 57.53; H, 4.81; N, 5.75.

The subsequent eluate gave (−)-3-[2-(4-chlorophenyl)isovaleroyloxy]-2-(2,4-dichlorophenyl)-1-(imidazol-1-yl)-2-propanol (3.1 g) as colorless prisms. Yield, 30.7%. M.P., 174°–175° C. $[α]_D^{27}$, −53.2° (C=1.0, MeOH).

Elementary analysis for $C_{23}H_{23}Cl_3N_2O_3$ (%): Calcd.: C, 57.34; H, 4.78; N, 5.82. Found: C, 57.29; H, 4.82; N, 5.80.

REFERENCE EXAMPLE 3

To a solution of (−)-3-[2-(4-chlorophenyl)isovaleroyloxy]-2-(2,4-dichlorophenyl)-1-(imidazol-1-yl)-2-propanol (6.85 g; M.P., 174°–175° C.) in ethanol (60 ml) was added a solution of sodium hydroxide (1.8 g) in water (10 ml), and the mixture was heated with stirring at 80° C. for 4 hours. The solvent was removed in vacuo and the residue was dissolved in 6N hydrochloric acid (70 ml). The acidic aqueous solution was washed with chloroform (20 ml×2) and then neutralized with a 28% aqueous ammonia solution. The resulting crystals were collected by filtration to give (−)-2-(2,4-dichlorophenyl)-1-(imidazol-1-yl)-2,3-propanediol. Yield, 3.6 g; 88%. M.P., 138.5°–141° C. $[α]_D^{24}$, −108.5° (C=1.0, MeOH).

REFERENCE EXAMPLE 4

To a solution of (+)-3-[2-(4-chlorophenyl)isovaleroyloxy]-2-(2,4-dichlorophenyl)-1-(imidazol-1-yl)-2-propanol (2.89 g; M.P., 145°–146.5° C.) in methanol (40 ml) was added a 20% aqueous potassium hydroxide solution (6 ml), and the mixture was stirred at room temperature for 3 hours. The solvent was removed in vacuo, and the oily residue was dissolved in 6N hydrochloric acid (30 ml). The acidic aqueous solution was washed with chloroform (20 ml×2) and then neutralized with a 28% aqueous ammonia solution. The resulting crystals were collected by filtration to give (+)-2-(2,4-dichlorophenyl)-1-(imidazol-1-yl)-2,3-propanediol. Yield, 1.51 g; 81%. M.P., 143° C. $[α]_D^{19}$, −113.1° (C=1.0, MeOH).

REFERENCE EXAMPLE 5

To an ice-cooled solution of (−)-2-(2,4-dichlorophenyl)-1-(imidazol-1-yl)-2,3-propanediol (5.4 g) in pyridine (50 ml) was added dropwise methanesulfonyl chloride (2.15 g). The reaction mixture was stirred at 0°–10° C. for 2 hours. An ice-cooled solution of 85.5% potassium hydroxide (3.7 g) in methanol (60 ml) was added dropwise thereto, and then the mixture was stirred at 0°–10° C. for 1 hour. The solvent was removed in vacuo, and the residue was extracted with chloroform. The extract was washed with water, dried over magnesium sulfate and evaporated to give a red oil. The oily residue was purified by chromatography on silica gel (60 g) with chloroform as a solvent and recrystallized from ether-hexane to give (−)-2-(2,4-dichlorophenyl)-2-(imidazol-1-yl)methyloxirane (4.3 g) as colorless needles. Yield, 84.6%. M.P., 107°–108.5° C. $[α]_D^{21.5}$, −8.4° (C=1.0, MeOH).

REFERENCE EXAMPLE 6

The reaction was carried out in the same manner as in Reference Example 5 but using (+)-2-(2,4-dichlorophenyl)-1-(imidazol-1-yl)-2,3-propanediol in place of the (−)-stereoisomer to give (+)-2-(2,4-dichlorophenyl)-2-(imidazol-1-yl)methyloxirane in 82.9% yield. M.P., 107°–108.5° C. $[α]_D^{24}$, +8.8° (C=1.0, MeOH).

What is claimed is:

1. An imidazolylcarboxylic acid compound of the formula:

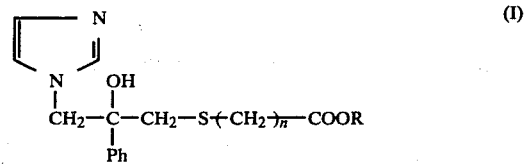

(I)

wherein Ph is an unsubstituted phenyl group or a phenyl group substituted with one or two halogen atoms, R is a hydrogen atom or a $C_1$–$C_8$ alkyl group and n is an integer of 1 to 8.

2. The compound according to claim 1, wherein Ph is a phenyl group substituted with one or two halogen atoms, R is a hydrogen atom or a $C_1$–$C_4$ alkyl group and n is an integer of 1 to 4.

3. The compound according to claim 2, which is ethyl 1-[2-(2,4-dichlorophenyl)-2-hydroxy-3-(imidazol-1-yl)propylthio]acetate.

4. The compound according to claim 2, which is 1-[2-(2,4-dichlorophenyl)-2-hydroxy-3-(imidazol-1-yl)propylthio]acetic acid.

5. The compound according to claim 2, which is ethyl 1-[2-(2,4-dichlorophenyl)-2-hydroxy-3-(imidazol-1-yl)propylthio]butyrate.

6. The compound according to claim 2, which is ethyl 1-[2-(2,4-dichlorophenyl)-2-hydroxy-3-(imidazol-1-yl)propylthio]pentanoate.

7. The compound according to claim 2, which is 1-[2-(2,4-dichlorophenyl)-2-hydroxy-3-(imidazol-1-yl)propylthio]pentanoic acid.

8. The compound according to claim 2, which is 1-[2-(2,4-dichlorophenyl)-2-hydroxy-3-(imidazol-1-yl)propylthio]butyric acid.

9. An imidazolylcarboxylic acid compound of the formula:

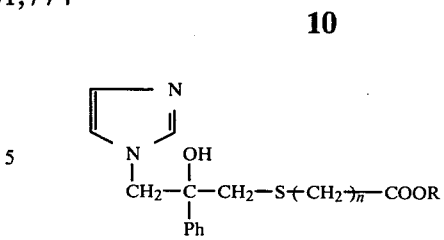

wherein Ph is a phenyl group substituted with one or two chlorine atoms, R is a hydrogen atom or a $C_1$-$C_4$ alkyl group and n is an integer of 1 to 4.

10. An antifungal composition which comprises as an active ingredient an antifungally effective amount of at least one of the imidazolylcarboxylic acid compounds according to claim 1 and at least one inert carrier or diluent.

11. A method for treating warm-blooded animals and human beings afflicted with fungi which comprises administering an effective antifungal amount of the composition of claim 10 thereto.

12. The method according to claim 11, wherein the dosage is from 10 mg to 5 g per day.

13. A method for inhibiting the growth of fungi on plants which comprises applying an effective antifungal amount of the composition of claim 10 to the area where the fungi are present.

* * * * *